United States Patent
Raneburger

(10) Patent No.: US 10,576,065 B2
(45) Date of Patent: Mar. 3, 2020

(54) PHARMACEUTICAL COMPOSITION CONTAINING RIFAXIMIN ALPHA AND DELTA

(71) Applicant: Sandoz AG, Basel (CH)

(72) Inventor: Johannes Raneburger, Kundl (AT)

(73) Assignee: Sandoz AG, Basel (CH)

( * ) Notice: Subject to any disclaimer, the term of this patent is extended or adjusted under 35 U.S.C. 154(b) by 55 days.

(21) Appl. No.: 15/738,663

(22) PCT Filed: Mar. 22, 2017

(86) PCT No.: PCT/EP2017/056797
§ 371 (c)(1),
(2) Date: Dec. 21, 2017

(87) PCT Pub. No.: WO2017/162725
PCT Pub. Date: Sep. 28, 2017

(65) Prior Publication Data
US 2018/0169076 A1 Jun. 21, 2018

(30) Foreign Application Priority Data
Mar. 24, 2016 (EP) .................................. 16162415

(51) Int. Cl.
*A61K 31/437* (2006.01)
*A61K 9/20* (2006.01)
*A61K 9/28* (2006.01)

(52) U.S. Cl.
CPC .......... *A61K 31/437* (2013.01); *A61K 9/2054* (2013.01); *A61K 9/2095* (2013.01); *A61K 9/2866* (2013.01)

(58) Field of Classification Search
USPC ........................................................ 514/279
See application file for complete search history.

(56) References Cited

U.S. PATENT DOCUMENTS

| 8,568,782 B2 * | 10/2013 | Viscomi | A61K 9/0095 424/490 |
| 9,018,225 B1 | 4/2015 | Hotha | |
| 2012/0128773 A1* | 5/2012 | Fischer | A61K 9/2081 424/465 |

FOREIGN PATENT DOCUMENTS

EP  1698630 A1  9/2006

OTHER PUBLICATIONS

Viscomi et. al. (CystEngComm (2008) 10:1074-1081). (Year: 2008).*
Observation submitted to the International Bureau by a third party concerning PCT/EP2017/056797, submitted Feb. 27, 2018, 38 pages.
International Search Report and Written Opinion for PCT/EP2017/056797 dated May 24, 2017.
Viscomi G.C. et al; Crystal forms of rifaximin and their effect on pharmaceutical properties; Crystengcomm Royal Society of Chemistry, Cambridge, GB; vol. 10, Jan. 1, 2008.
Blandizzi et al, Dovepress Drug Design, Development and Therapy Impact of crystal polymorphism on the systemic bioavailability of rifaximin, an antibiotic acting locally in the gastrointestinal tract, in healthy volunteers, 2015.
Braga et al, Electronic Supplementary Material, The structure-property relationship of four crystal forms of rifaximin, The Royal Society of Chemistry, 2012.
Braga et al, The structure-property relationship of four crystal forms of rifaximin, CrystEngComm, Jun. 8, 2012.

* cited by examiner

*Primary Examiner* — Marcos L Sznaidman
(74) *Attorney, Agent, or Firm* — Luedeka Neely Group, P.C.

(57) ABSTRACT

The present invention relates to a pharmaceutical composition containing rifaximin in the form of two different polymorphs as well as a method of preparing the same.

13 Claims, 2 Drawing Sheets

Figure 1: XRPD of form alpha:
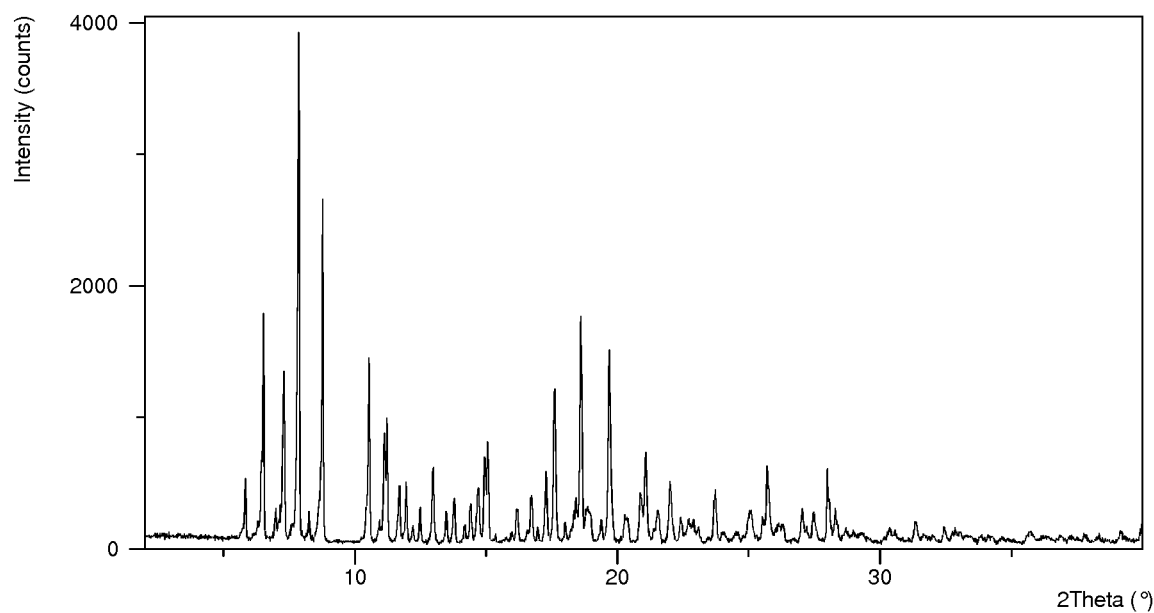
Figure 2: XRPD of form delta:
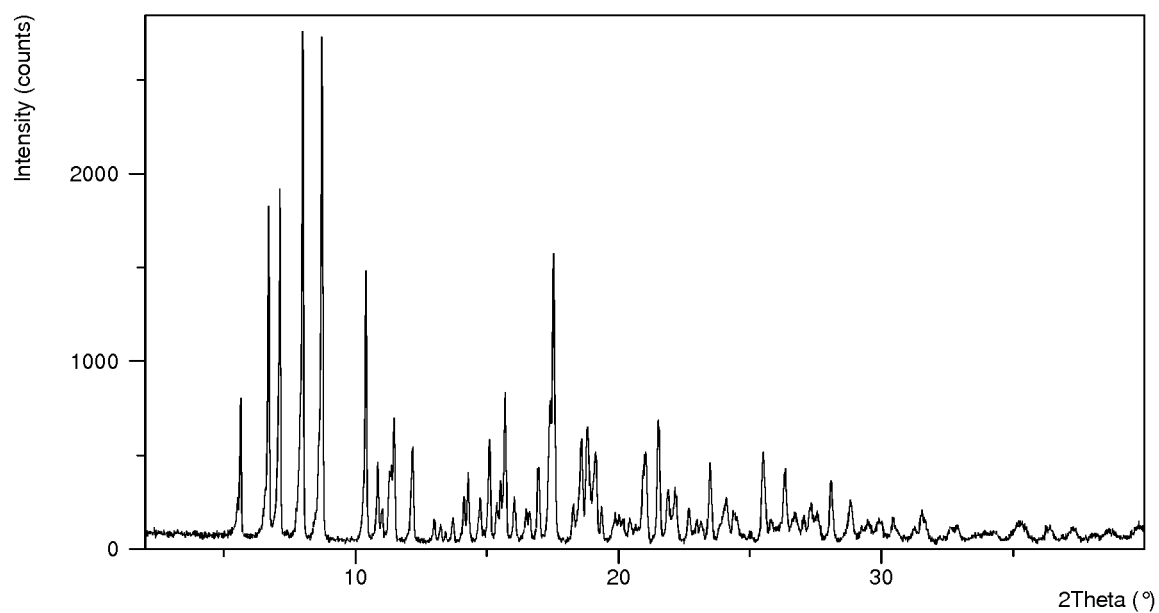

Figure 3: Disintegrated particles of Example 1: Microcrystalline cellulose and rifaximin still sticking together/adhering as granules
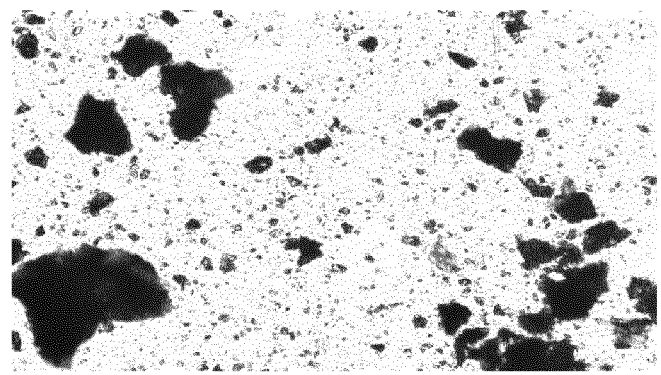
Figure 4: Disintegrated particles of Comparative Example 1: Microcrystalline cellulose and rifaximin particles are separated
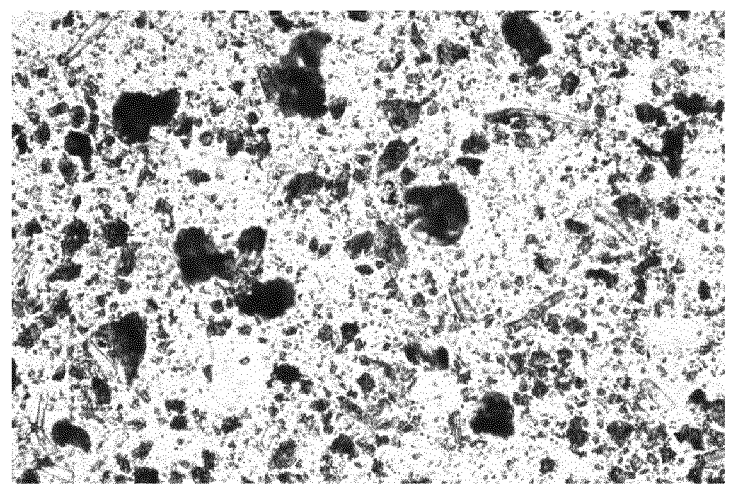

PHARMACEUTICAL COMPOSITION CONTAINING RIFAXIMIN ALPHA AND DELTA

This application is a Section 371 national phase entry of PCT application PCT/EP2017/056797, filed Mar. 22, 2017. This application also claims the benefit of the earlier filing date of European patent application 16162415.0, filed Mar. 24, 2016.

The present invention relates to a pharmaceutical composition containing two different polymorphs of rifaximin and a method of preparing the same.

BACKGROUND OF THE INVENTION

Rifaximin is a semisynthetic derivative of rifamycin, wherein rifaximin is an oral, bactericidal broad-spectrum antibiotic. The IUPAC name of rifaximin is (2S,16Z,18E,20S,21S,22R,23R,24R,25S,26S,27S,28E)-5,6,21,23,25-pentahydroxy-27-methoxy-2,4,11,16,20,22,24,26-octamethyl-2,7-(epoxypenta-deca[1,11,13]trienimino) benzofuro[4,5-e]pyrido[1,2-a]-benzimida-zole-1,15(2H)-dione,25-acetate and the compound is represented by the following formula

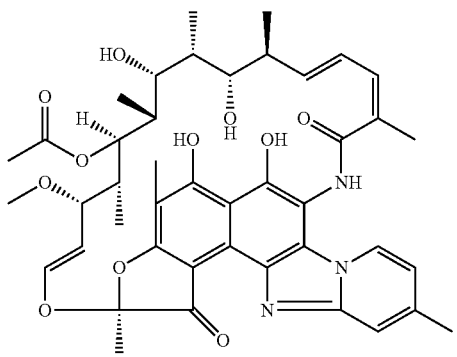

Rifaximin can be used in the treatment of bacterial infections of the gastrointestinal tract, for example in the treatment of traveler's diarrhea. Further, the active pharmaceutical agent can be used in the treatment or prevention of hepatic encephalopathy and is said to be efficacious in relieving chronic functional symptoms of bloating and flatulence that are common in irritable bowel syndrome (IBS) and Morbus Crohn.

Rifaximin is reported to show its efficiency almost exclusively locally, i.e. rifaximin exerts its effects at the site of application, wherein this site of application is the gastrointestinal tract.

Several polymorphic forms of rifaximin are described, wherein these polymorphic forms can convert into each other. Viscomi G. C. et al., "Crystal forms of rifaximin and their effect on pharmaceutical properties", Royal Society of Chemistry, CrystEngComm, 10 (2008), pages 1074-1081, show in FIG. 4 a diagram in which the relationship between the various polymorphic forms of rifaximin is scheduled. The conversion of these different forms into each other inter alia seems to be related to the amount of moisture, in particular water, contained in the corresponding forms. As can be seen from Table 7 of said document, the bioavailabilities of the various forms of rifaximin differ from each other. For example, with reference to the corresponding $C_{max}$ and AUC values, rifaximin in form γ or in form δ are reported to show a far higher bioavailability (in dogs) than rifaximin in the other polymorphic forms:

| Form | $C_{max}$ [ng/ml] | AUC [ng/ml × h] |
|---|---|---|
| Alpha | 2.6 | 17 |
| Beta | 1.1 | 12 |
| Gamma | 1,085.1 | 4,894 |
| Delta | 308.3 | 830 |
| Epsilon | 6.9 | 77 |

With reference to the above-mentioned local effectiveness of rifaximin, a low bioavailability is desirable. As can be seen from the above-mentioned table, rifaximin in polymorphic forms β and ε are reported to show a rather poor bioavailability. However, form β of rifaximin is reported to contain water in an amount of 6 to 40 wt %. Drugs having such a high water content are usually regarded as disadvantageous since they usually have inferior stability and processability properties. Further, it is difficult to prepare form ε of rifaximin since it is reported to be obtained only under very specific conditions.

Further, Blandizzi C. et al., "Impact of crystal polymorphism on the systemic bioavailability of rifaximin, an antibiotic acting locally in the gastrointestinal tract, in healthy volunteers", Drug Design, Development and Therapy, 9 (2015) pages 1-11, compare the bioavailability of rifaximin in a human after the administration of rifaximin in amorphous form and rifaximin in polymorphic form α, each in the amounts of 200 mg and 400 mg. In table 2 of said document it is shown that the $C_{max}$ value and AUC values are significantly higher when rifaximin in amorphous form is administered:

| Dosage | $C_{max}$ [ng/ml] | AUC [ng/ml × h] |
|---|---|---|
| 200 mg amorphous | 3.70 | 16.13 |
| 200 mg alpha | 1.59 | 5.77 |
| 400 mg amorphous | 15.01 | 68.80 |
| 400 mg alpha | 3.54 | 13.03 |

In view of the above, due to the reaction mechanism of rifaximin, there is still a need of a pharmaceutical composition containing rifaximin with a bioavailability being as low as possible. Hence, it was an object of the present invention to overcome the drawbacks of the above-mentioned prior art.

In particular, it was an object of the present invention to provide a pharmaceutical composition containing rifaximin showing minimal $C_{max}$ and AUC values while at the same time achieving a sufficient local concentration in the gastrointestinal tract. Further, it was an object to provide a pharmaceutical composition containing rifaximin wherein the minimal $C_{max}$ and AUC values can be achieved even after storage of the pharmaceutical composition. In addition, a pharmaceutical composition with good processability should be provided, i.e. the pharmaceutical composition should be processed into an oral dosage form, preferably a tablet, without the need of a time and cost-consuming preparation method.

According to the present invention, the above objectives are unexpectedly achieved by a pharmaceutical composition comprising two specific polymorphic forms of rifaximin being present in a specific molar ratio.

Thus, a subject of the invention is a pharmaceutical composition comprising (A) rifaximin in polymorphic form α,
(D) rifaximin in polymorphic form δ,
wherein the molar ratio of (A) rifaximin in polymorphic form α to (D) rifaximin in polymorphic form δ is from 9:1 to 1:9.

A further subject of the invention is the method for preparing a tablet according to the present invention comprising the steps of
(i) providing (A) rifaximin in polymorphic form α and (D) rifaximin in polymorphic form δ, wherein the molar ratio of (A) rifaximin in polymorphic form α to (D) rifaximin in polymorphic form δ is from 9:1 to 1:9 and optionally one or more further excipients
(ii) optionally dry granulating the mixture of step (i) and optionally one or more further excipients
(iii) compressing the mixture from step (i) or the granulates from step (ii) and optionally further excipients into a tablet.

It was unexpectedly found that the pharmaceutical composition of the present invention containing rifaximin in polymorphic forms α and δ in a specific molar ratio shows an advantageously low $C_{max}$ value. Thus, a reliable and poor systemic absorbance of the active pharmaceutical ingredient is achieved. The achieved $C_{max}$ value is even lower than the one of rifaximin in pure polymorphic form α. Further, the pharmaceutical composition of the present invention is easy to handle and can for example be further processed by direct compression into a tablet.

DETAILED DESCRIPTION OF THE INVENTION

The present invention relates to a pharmaceutical composition comprising (A) rifaximin in polymorphic form α and (D) rifaximin in polymorphic form δ, wherein the molar ratio of (A) rifaximin in polymorphic form α to (D) rifaximin in polymorphic form δ is from 9:1 to 1:9.

As indicated above, rifaximin can be present in different polymorphic forms. These polymorphic forms can be different crystalline forms and/or the result of stoichiometric and non-stoichiometric hydration or solvation.

A polymorphic form can be represented by one or more, preferably at least three, specific diffraction peaks in X-ray powder diffraction (XRPD).

In the present application, the XRPD is determined as described below in the experimental section.

Further, unless indicated otherwise, XRPD peaks are reported as degrees 2θ values with a standard error of ±0.2 degrees 2θ.

Compound (A) of the present application is rifaximin in form α having diffraction peaks in the XRPD at 11.7, 13.0 and 19.6 degrees 2θ (±0.2 degrees 2θ). These peaks may be regraded as particularly characteristic diffraction peaks for rifaximin in polymorphic form α. Preferably, further peaks occur at 6.5, 7.3, 7.9, 8.7, 10.5, 11.1, 17.6, 18.6, 21.1, 21.5 and 22.0 degrees 2θ (±0.2 degrees 2θ). A respective XRPD of form α is shown in FIG. 1.

Compound (D) of the present application is rifaximin in form δ having diffraction peaks in the XRPD at 5.6, 12.2 and 17.0 degrees 2θ (±0.2 degrees 2θ). These peaks may be regraded as particularly characteristic diffraction peaks for rifaximin in polymorphic form δ. Preferably, further peaks occur at 6.7, 7.1, 8.0, 8.7, 10.4, 10.8, 11.3, 17.4, 17.5, 18.6, 18.8, 19.1, 21.0 and 21.5 degrees 2θ (±0.2 degrees 2θ). A respective XRPD of form δ is shown in FIG. 2.

In a preferred embodiment the composition of the present invention may comprise, apart from rifaximin in polymorphic forms α and δ, other polymorphic form(s) of rifaximin. Preferably, the other polymorphic form(s) of rifaximin are present in an amount of less than 5%, more preferably less than 4%, still more preferably less than 3%, in particular less than 2%, based on the amount of rifaximin. In a preferred embodiment other polymorphic forms are either absent or present in such low amounts that they cannot be detected by XPRD.

The pharmaceutical composition of the present invention comprises (A) rifaximin in polymorphic form α and (D) rifaximin in polymorphic form δ in a molar ratio of 9:1 to 1:9, preferably 8:1 to 1:7, more preferably 6:1 to 1:5, even more preferably 5:1 to 1:3. In a particularly preferred embodiment the pharmaceutical composition of the present invention comprises (A) rifaximin in polymorphic form α and (D) rifaximin in polymorphic form δ in a molar ratio of about 3:1.

The molar ratio of polymorphs, in particular the alpha/delta molar ratio, can preferably be determined by the "Rietveld Analysis" of powder X-ray diffraction data, wherein the diffraction data is obtained as described below in the experimental section.

In a further preferred embodiment the pharmaceutical composition can contain a total amount of rifaximin of 200 to 550 mg.

The total amount of rifaximin is the sum of all polymorphic forms of rifaximin, such as at least polymorphic forms α and δ of rifaximin.

In a particularly preferred embodiment the pharmaceutical composition contains rifaximin in a total amount of about 200 mg.

In an alternatively particularly preferred embodiment the pharmaceutical composition contains rifaximin in a total amount of about 550 mg.

It is further preferred that upon administration of the pharmaceutical composition containing rifaximin in a total amount of 550 mg the $C_{max}$ of rifaximin is less than 1.5 ng/ml.

$C_{max}$ is a term which is used in pharmacokinetics and refers to the maximum serum or plasma concentration, wherein said maximum concentration is achieved by the administration of a definite amount of a drug in a specified compartment or test area of the human body, in particular prior to the administration of a second dose. In the case of oral administration, $C_{max}$ is dependent on the extent and the rate of drug absorption and the disposition profile of the drug. As described before, due to the reaction mechanism of rifaximin, a low $C_{max}/AUC$ is desirable. Preferably, in the present invention the $C_{max}/AUC$ values are determined as described below in the experimental section.

It is further preferred that upon administration of the pharmaceutical composition containing rifaximin in a total amount of 550 mg the $C_{max}$ of rifaximin is less than 1.4 ng/ml, preferably less than 1.3 ng/ml, more preferably less than 1.2 ng/ml, even more preferably less than 1.1 ng/ml, in particular less than 1.0 ng/ml.

In a preferred embodiment the pharmaceutical composition of the present invention comprises a rifaximin mixture of alpha and delta, wherein the rifaximin mixture has a water content of 1.5 wt. % to 5.5 wt. % based on the total amount of rifaximin. It is more preferred that the rifaximin mixture contains water in an amount of 2.0 wt. % to 4.5 wt. %, even more preferably 2.2 wt. % to 3.5 wt. %, especially about 2.5 wt. %, based on the total amount of rifaximin.

The water content can be preferably determined as described below in the experimental part.

It turned out unexpectedly that the use of a rifaximin having the before-mentioned water content ensures that upon administration bioavailability was advantageously low and the workability (e.g. compressability, flowability) of the pharmaceutical composition was good. It is believed that these properties are particularly superior if excipients as described below are used in the formulation.

It is further preferred that the pharmaceutical composition of the present invention further comprises one or more pharmaceutically acceptable excipients.

Generally, suitable pharmaceutical excipients are for example disclosed in "Lexikon der Hilfsstoffe für Pharmazie, Kosmetik and angrenzende Gebiete", published by H. P. Fielder, $4^{th}$ Edition, and "Handbook of Pharmaceutical Excipients", $3^{rd}$ Edition, published by A. H. Kibbe, American Pharmaceutical Association, Washington, USA, and Pharmaceutical Press, London.

Pharmaceutically acceptable excipient(s) can for example be fillers, disintegrants, glidants and lubricants.

Fillers can be used to increase the bulk volume and weight of a low-dose drug to a limit at which a pharmaceutical dosage form can be formed. Fillers may fulfil several requirements, such as being chemically inert, non-hygroscopic and biocompatible. Examples of fillers are microcrystalline cellulose, silicified microcrystalline cellulose, dextrose, lactose, sucrose, glucose, mannitol, calcium carbonate, magnesium aluminum silicate and others. In particular, microcrystalline cellulose (MCC) is used as a suitable filler.

In a preferred embodiment the filler used in the composition of the present invention has a water content of 2.5 to 5 wt. %, preferably of 3.0 to 4.5 wt. %.

In the present invention, the filler can be present in an amount of 0 wt. % to 60 wt %, preferably 10 wt. % to 45 wt. %, more preferably 20 wt. % to 40 wt. %, in particular 28 wt. % to 35 wt. %, based on the total weight of the pharmaceutical composition. It was found that the combination of rifaximin alpha/delta with suitable types/amounts of fillers lead to a composition with particular superior properties.

Disintegrants are compounds which enhance the ability of the dosage form, preferably the ability of the tablet, to break into smaller fragments when in contact with a liquid, preferably water. Suitable disintegrants are for example croscarmellose sodium, sodium carboxymethyl starch, cross-linked polyvinylpyrrolidone (crospovidone), sodium carboxymethylglycolate (=sodium starch glycolate) and sodium bicarbonate, preferably cross-linked polyvinylpyrrolidone (crospovidone) and sodium carboxymethylglycolate. Sodium starch glycolate is used in a preferred embodiment. The disintegrant can be present in an amount of 0 to 20 wt. %, preferably in an amount of 1 wt. % to 15 wt. %, based on the total weight of the pharmaceutical composition.

Glidants can be used to improve the flowability. Suitable glidants are for example colloidal silicon dioxide, talcum or mixtures thereof. The glidant can be present in an amount of 0 to 8 wt. %, preferably in an amount of 0.1 wt. % to 3 wt. %, based on the total weight of the composition.

Lubricants generally can be regarded as substances which are suitable to reduce friction, such as static friction, sliding friction and rolling friction. In particular, lubricants reduce the shearing forces occurring on the borderline between tablet and mould, especially the sliding friction found during tablet pressing between the punch moving up and down in the die and the die wall on the one hand and between the edge of the tablet and the die wall on the other hand. Lubricants can for example be alkaline earth metal salts of fatty acids, such as magnesium stearate. Alternatively, lubricants can be esters, preferably diesters of glycerol with fatty acids, such as glycerol palmitostearate. Glycerol palmitostearate is used in a preferred embodiment. The lubricant can be present for example in an amount of 0 to 5 wt. %, preferably in an amount of 0.5 wt. % to 2.5 wt. %, based on the total weight of the composition.

In a preferred embodiment the composition of the present invention comprises:
45 wt. % to 75 wt. % of components (A) and (D), preferably 50 wt. % to 65 wt. % of components (A) and (D), in particular 54 wt. % to 60 wt. % of components (A) and (D), wherein the rifaximin preferably has a water content as described above, and
10 wt. % to 45 wt. % filler, preferably 20 wt. % to 40 wt. % filler, in particular 28 wt. % to 35 wt. % filler, wherein the filler preferably is MCC,
wherein wt. % is based on the total weight of the composition.

It is particularly preferred that such a composition is dry-granulated as described below.

In another preferred embodiment the composition of the present invention comprises:
45 wt. % to 75 wt. % of components (A) and (D), preferably 50 wt. % to 65 wt. % of components (A) and (D), in particular 54 wt. % to 60 wt. % of components (A) and (D),
10 wt. % to 45 wt. % filler, preferably 20 wt. % to 40 wt. % filler, in particular 28 wt. % to 35 wt. % filler, e.g. MCC,
0 to 10 wt. % disintegrant, preferably 1.5 wt. % to 8 wt. % disintegrant, in particular 2.5 wt. % to 6 wt. % disintegrant, e.g. sodium starch glycolate
0 to 5 wt. % glidant, preferably 0.5 wt. % to 4.5 wt. % glidant, in particular 1 wt. % to 3 wt. % glidant, e.g. talc and colloidal solicon dioxide
0 to 5 wt. % lubricant, preferably 0.3 wt. % to 4 wt. % lubricant, in particular 0.6 wt. % to 2 wt. % lubricant, e.g. glycerol palmitostearate,
wherein component (A), rifaximin in polymorphic form α, and component (D), rifaximin in polymorphic form δ, are present in a molar ratio of 9:1 to 1:9 and wherein wt. % is based on the total weight of the composition.

The pharmaceutical composition can preferably be present as an oral doasage form, such as a capsule or tablet, preferably a tablet. In other words, another subject of the present invention is an oral dosage form comprising the composition of the present invention as described above and below.

In case that the oral dosage form is a tablet, the tablet can preferably be coated or uncoated, preferably coated, more preferably film-coated.

Generally, film coatings that do not affect the release of the active agent(s) and film coatings affecting the release of the active agent(s) can be employed with the tablets according to the invention. The film coatings that do not affect the release of the active agent(s) are preferred.

Preferred examples of film coatings which do not affect the release of the active ingredient can be those including poly(meth)acrylate, methylcellulose (MC), hydroxypropyl methylcellulose (HPMC), hydroxypropyl cellulose (HPC), hydroxyethyl cellulose (HEC), polyvinylpyrrolidone (PVP), polyvinylalcohol (PVA) and mixtures thereof. More preferred is hydroxypropyl methylcellulose (HPMC). These polymers can have a weight-average molecular weight of 10,000 to 150,000 g/mol.

In a preferred embodiment the film can have a thickness of 2 µm to 150 preferably 10 to 100 more preferably 20 to 60 µm.

The preferred coating may comprise a film-forming agent and one or more of the following: lubricant, surfactant, glidant, pigment and water.

In a preferred embodiment of the present invention the dosage form of the present invention is packed by a suitable packaging material. The packaging material preferably reduces or prevents water exchange between the pharmaceutical composition of the present invention and the environment. For example, if the dosage form is in the form of tablets or capsules, suitable blister pack materials can be used. The blister pack may comprise a cavity or pocket, preferably containing a thermoformed plastic. This usually has as a backing a lidding seal containing an aluminum and/or plastic foil. Further, if the composition is in form of a granulate, suitable sachets can be used.

In a particularly preferred embodiment the pharmaceutical composition or the dosage form of the present invention is packed by a material having a water vapor permeability of 0.001 to 0.15 g/m$^2$/day at 38° C./5%/90% RH, preferably of 0.01 to 0.12 g/m$^2$/day at 38° C./5%/90% RH, in particular 0.05 to 0.10 g/m$^2$/day at 38° C./5%/90% RH, wherein said water vapor permeability is determined according to ASTM F1249-13. Preferably, a Permatran-W Model 3/33 device is used. The measurement is preferably carried out at 38° C. Further, preferably the humidity in the dry chamber is 5% relative humidity (=RH), whereas the humidity in the wet chamber is 90% RH.

In a preferred embodiment the packing material comprises layered sheets which can be thermoformed containing one or more layers. In a preferred embodiment the packing material can be a composite material, e.g. co-extruded composite material, e.g. a polyamide-alumina-polyvinyl chloride composite material which is also referred to as Nylon®-Alu-PVC.

In a preferred embodiment the packaging material has a thickness of 1 µm to 1 mm. In case of a blister pack the thermoformed plastic pocket preferably has a thickness of 100 to 1000 µm, more preferably of 150 to 800 µm. Further, the backing foil usually has a thickness of 10 to 150 µm, more preferably from 15 to 100 µm.

A further subject of the present invention is a method for preparing a tablet according to the invention comprising the steps of
(i) providing (A) rifaximin in polymorphic form α and (D) rifaximin in polymorphic form δ, wherein the molar ratio of component (A) to (D) is from 9:1 to 1:9 and optionally one or more further excipient(s),
(ii) optionally dry granulating the mixture of step (i) and one or more further excipients, and
(iii) compressing the mixture from step (i) or the granules from step (ii) and optionally further excipients into a tablet
(iv) optionally film coating the tablet and
(v) optionally packaging the tablet.

As far as (A) rifaximin in polymorphic form α and (D) rifaximin in polymorphic form δ and excipients are concerned for the present method, the same applies as to the before-mentioned pharmaceutical composition.

In step (i), (A) rifaximin in polymorphic form α and (D) rifaximin in polymorphic form δ being present in the above-mentioned molar ratio are provided.

It is preferred that rifaximin (A) in polymorphic form α and rifaximin (D) in polymorphic form δ and optionally one or more further excipient(s) can be blended in order to provide a composition having a homogenous distribution of rifaximin (A) in polymorphic form α and rifaximin (D) in polymorphic form δ within the resulting oral dosage form. It is particularly preferred that in step (i) rifaximin (A) in polymorphic form α and rifaximin (D) in polymorphic form δ can be blended with a filler, a disintegrant and a glidant. Blending can be carried out with conventional mixing devices, e.g. in a free-fall mixer. Blending can be carried out e.g. for 1 minute to 30 minutes, preferably for 2 minutes to less than 10 minutes.

It is further preferred that the blend containing rifaximin (A) in polymorphic form α and rifaximin (D) in polymorphic form δ and optionally one or more further excipient(s) can be sieved, preferably with a sieve having a mesh size of 25 to 1000 µm, preferably 50 to 800 µm, especially 100 to 600 µm.

In optional step (ii) the mixture from step (i) and optionally one or more further excipient(s) can be dry-granulated. In a preferred embodiment the one or more further excipient(s) can preferably be a lubricant.

"Dry" is usually understood to mean that the step is carried out in the absence of a liquid, in particular in the absence of water. "Granulating" is generally understood to mean the formation of relatively coarse or granular aggregate material as a powder by assembling and/or aggregating finer powder particles (agglomerate formation or build-up granulation) and/or the formation of finer granules by breaking up coarser aggregates (disintegration or break-down granulation). Dry granulation can preferably be carried out by using pressure or temperature. In a preferred embodiment of the invention, granulating the mixture from step (i) can be performed for example by "slugging", i.e. by using a large heavy-duty rotary press and breaking up the slugs into granulates with a hammer mill or by roller compaction using for example roller compactors by Powtec or Alexanderwerk. The granules are then optionally screened.

In step (iii) the mixture of step (i) or the granules of step (ii) and optionally further excipients can be compressed into a tablet. Compressing the mixture of step (i) or the granules from step (ii) into a tablet can preferably be carried out by compressing said formulation on a rotary press. The main compression force can range from 1 to 50 kN, preferably from 3 to 40 kN. The resulting tablets can have a hardness of 30 to 400 N, more preferably of 50 to 250 N, particularly preferably of 30 to 180 N, more preferably 40 to 150 N, wherein the hardness can be measured according to Ph. Eur. 6.0, Chapter 2.9.8.

In a preferred embodiment steps (i), (ii) and (iii) can be performed under non-humid conditions. In particular, these steps can be performed at a temperature of 0° C. to 30° C., preferably of 10° C. to 25° C. Further, said process is preferably performed at 0 to 40% RH or less, preferably at 5 to 20% RH.

Further, the dosage form, preferably the tablet, of the invention preferably has a content uniformity, i.e. a content of active agent(s), which lies within the concentration of 90 to 110%, preferably 95 to 105%, especially preferred from 98 to 102% of the average content of the active agent(s). The "content uniformity" is determined with a test in accordance with Ph. Eur., 6.0, Chapter 2.9.6. According to this test, the content of the active agent of each individual tablet out of 20 tablets must lie between 90 and 110%, preferably between 95 and 105%, especially between 98 and 102% of the average content of the active agent(s). Therefore, the content of the active agent(s) in each tablet of the invention differs from the average content of the active agent(s) by at most 10%, preferably at most 5% and especially at most 2%.

In addition, the resulting tablet preferably has a friability of less than 5%, particularly preferably less than 2%, especially less than 1%. The friability is determined in accordance with Ph. Eur., 6.0, Chapter 2.9.7. The friability of tablets generally refers to tablets without coating.

In a further optional step (iv) the tablets from step (iii) can preferably be film coated, wherein film coatings such as Opadry II can be used.

In a further optional step (v) the tablets from step (iii) or (iv) can be packaged. Preferably, the materials as described above are used.

In an alternative production process the required molar ratio of rifaximin alpha:delta can be obtained by storing the composition under specific conditions. Hence, a further subject of the present invention is a method for preparing a tablet according to the invention comprising the steps of
(i') providing (A) rifaximin in polymorphic form α having a water content of 2 to 4.5 wt. % and optionally one or more further excipient(s),
(ii') optionally dry granulating the mixture of step (i') and one or more further excipients,
(iii') compressing the mixture from step (i') or the granules from step (ii') and optionally further excipients into a tablet and
(iv') storing the composition under sealed conditions at 25° C. for 2 to 3 months.

The term "sealed" preferably indicates that there is no air-exchange during storage. In a preferred embodiment the tablets are stored under packed conditions, wherein a package material as described above is used.

In other words, the provision of components (A) and (D) according to the present invention can alternatively be achieved by storing crystalline rifaximin alpha having a water content of 2 to 4.5 wt. % at 25° C. under sealed conditions for about 3 months (step iv'). In step (iv') the term "sealed" preferably indicates that there is no air-exchange during storage. In a preferred embodiment the tablets are stored under packed conditions, wherein a package material as described above is used.

With regard to steps (i') to (iii') the explanations given above apply.

The invention shall be illustrated by the following examples.

EXAMPLES

1. Analytical Methods 1.1 XPRD & Rietveld Refinement

Parameters XRPD: X-ray powder diffraction patterns (XRPD) were obtained with an X'Pert PRO diffractometer (PANalytical, Almelo, Netherlands) equipped with a theta/theta coupled goniometer in transmission geometry, programmable XYZ stage with well plate holder, Cu-Kα1,2 radiation source (wavelength 0.15419 nm) with a focusing mirror, a 0.5° divergence slit, a 0.04 rad Soller slit collimator and a 0.5° anti-scattering slit on the incident beam side, a 1.4 mm anti-scattering slit, a 0.02 rad Soller slit collimator, a Ni-filter and a 1d-PIXcel solid state line detector (255 channels) on the diffracted beam side. The patterns were recorded at a tube voltage of 45 kV, tube current of 40 mA, applying a stepsize of 0.013° 2-theta with an exposure time of 40 s per step in the angular range of 2° to 40° 2-Theta at ambient conditions, preferably at 25° C. and 20% RH. A typical precision of the 2-Theta values is in the range of about ±0.2° 2-Theta. Thus a diffraction peak that appears at 6.6° 2-Theta can appear between 6.4 and 6.8° 2-Theta on most X-ray diffractometers under standard conditions.

Rietveld refinement of the sample's phase composition was done by Highscore 4.1 from Panalytical. Crystal structures were received from the Cambridge structural database as described in Braga et al., CrystEngComm, 2012, 14, 6404-6411. Atom positions were taken directly from single-crystal structure and were not refined; no correction is attempted for the fact that the single-crystal structures were measured at 25° C. An overall isotropic Debye-Waller factor was refined with the same value for all phases. Refined parameters were the zero point, scaling factors, lattice parameters, 5 background points, 3 peak-width parameters and 1 parameter of anisotropic broadening. Preferred orientation correction in hkl 1 1 0 is refined for the main phases with the 1-parameter March model.

1.2 Water Content According to Karl Fischer

The water content was determined according to Ph. Eur 6.0, 2.5.12 Method A, wherein an Excellence Titrator T70 (Mettler Toledo) was used.

Preferably, the following measurement parameters can be used:

| | |
|---|---|
| Weight sample: | 200 mg |
| Density: | 1.0 g/mL |
| Temperature: | 25° C. |
| Titration agent: | KF1-comp 5 |
| Nominal concentration: | 5 mg/mL |
| Weight | 0.015 g |
| Temperature: | 25° C. |
| Duration for mixing: | 30 sec |
| Sensor type: | polarised |
| Sensor | DM 143-SC |
| Unit: | mV |
| Indication | voltametric |
| Ipol | 24.0 µA |
| Stirring: | 35% |
| Regulation: | |
| Endpoint: | 100.0 mV |
| Control band: | 400.0 mV |
| Dosing rate (max): | 5 mL/min |
| Dosing rate (min): | 80 µL/min |
| Stop | |
| Type: | Driftstop absolut |
| Drift | 25 µg/min |
| at Vmax: | 50 mL |
| Time (min.) | 0 |
| Time (max.) | ∞ |
| Calculation | |
| Result: | Content |
| Result (unit) | % |
| Formula: | R1 = (VEQ · CONC-TIME · DRIFT/1000) · C/m |
| Constant C = | 0.1 |

The sample was prepared and weighted in a glove box with less than 5% RH. For determination of the water content 5 samples were measured and the average of the corresponding values was calculated.

1.3 Measurement of Pharmacokinetic Parameters
a) Subjects

Overall, the study was carried out with 42 people. Among them 13 healthy male volunteers were chosen. The age was between 27 and 55 years, the body weight was between 65 and 99 kg. Further, 29 healthy female volunteers were chosen. The age was between 23 and 55 years, the body weight was between 51 and 85 kg.

The formulation to be tested was administered in fasted state.

b) Determination of Values

Plasma concentrations of rifaximin in subject samples were measured utilizing Analyst® Software Version 1.6.2, according to an achiral, liquid chromatographic tandem mass spectrometric detection (LC-MS/MS) method (PMRI-1364-12 v.00) developed and validated at the Bioanalytical Laboratory of Pharma Medica Research Inc. The method involved a liquid-liquid extraction. The standard calibration range was from 0.0100 to 5.00 ng/mL using a plasma sample volume of 0.200 mL. Plasma samples were extracted under basic conditions with a mixture of organic solvents; the organic phase was dried and reconstituted in reconstitution solvent. Sample analysis was conducted using reversed phase chromatography.

Rifaximin was analyzed in the SCIEX API 4000 mass spectrometer using positive ion scan mode with a parent-daughter mass to charge ion transition of 786-754. Similarly, the internal standard for rifaximin was analyzed using a parent-daughter mass to charge transition of 792-760. The expected retention time for rifaximin and the internal standard is approximately 1.2 minutes. Although the retention time of rifaximin and the internal standard is the same, the MS/MS technique allows distinguishing between the two molecules for quantitation, as they have different parent-daughter ion transitions.

$C_{max}$: Defined as maximum measured rifaximin concentration over the sampling period AUCt: Defined as area under the rifaximin concentration versus time curve, from time zero (0) to the time of the last measurable rifaximin concentration (t), as calculated by the linear trapezoidal method.

AUCinf: Defined as area under the rifaximin concentration versus time curve from time zero to infinity. AUCinf=AUCt+Ct/Kel, where Ct is the last measurable rifaximin concentration.

2. Preparation of Tablets

Example 1

A rifaximin composition comprising polymorphic forms α and δ, having a molar ratio of rifaximin α to rifaximin δ of 3:1 and a water content of 32 wt. %, was provided. The composition was mixed together with microcrystalline cellulose, colloidal silicon dioxide and sodium starch glycolate for 15 minutes at 23 rpm in a "Heidolph Reax 2 Überkopfmischer". The mixture was dry granulated. Talc and glycerol palmitostearate were added to the granules and the mixture was blended. The final blend was compressed on a press and the resulting tablets were film coated with Opadry II 85F540027 such that the resulting tablets each contained

| | |
|---|---|
| Rifaximin | 550 mg |
| Microcrystalline cellulose | 315 mg |
| Colloidal silicon dioxide | 12.5 mg |
| Sodium starch glycolate | 38.5 mg |
| Talc | 10.5 mg |
| Glycerol palmitostearate | 13.5 mg |
| Opadry II 85F540027 | 23 mg. |

The pharmacokinetic results upon administration are shown below.

Examples 2 and 3

Further tablets according to Example 1 were prepared, wherein the molar ratio of rifaximin in polymorphic form α to rifaximin in polymorphic form δ were 2) 5.5:1
3) 1:2.5.

The water content of the rifaximin composition in Examples 2 and 3 was 2.4 wt. % and 4.1 wt. %, respectively The pharmacokinetic results upon administration are shown below.

3. Prior Art Formulations

Film coated tablets containing 400 mg rifaximin in pure polymorphic form α and in amorphous form were examined by Blandizzi C. et al., see Drug Design, Development and Therapy, 9 (2015) pages 1-11.

4. Pharmacokinetic Results

The pharmacokinetic data can be summarized as follows:

| Example | mg | $C_{max}$ [ng/ml] | AUCt [ng/ml × h] |
|---|---|---|---|
| 1 | 550 | 0.53 | 4.9 |
| 2 | 550 | 0.4 | 4.2 |
| 3 | 550 | 0.6 | 5.5 |
| Prior art alpha | 400 | 3.54 | 13.03 |
| Prior art amorphous | 400 | 15.01 | 68.80 |

As can be seen from these Examples, even though the present composition contains more active agent than the one according to Blandizzi C. et al., the $C_{max}$ and AUC values upon administration of the tablet according the present invention are significantly lower.

5. Formulation Properties

Comparative Example 1

Further tablets according to Example 1 were prepared, wherein the molar ratio of rifaximin in polymorphic form α to rifaximin in polymorphic form δ was >10:1 and the water content was 1.2 wt. %.

The formulation properties of Example 1 and Comparative Example 1 were examined. Both formulations were dry-granulated as described in Example 1. Subsequently, the particle properties resulting from disintegration in water were examined.

FIG. 3 shows the disintegrated tablet according to inventive Example 1. It can be seen that the API sticks closely to the surface of the filler MCC.

FIG. 4 shows the disintegrated tablet according to Comparative Example 1. It can be seen that the API no longer sticks to the surface of the filler MCC. Instead, the API is present in form of small particles having a high surface area (and thus leading to an undesirable high absorption).

The invention claimed is:

1. Pharmaceutical composition comprising
   (A) rifaximin in polymorphic form α
   (D) rifaximin in polymorphic form δ,
   wherein the molar ratio of (A) rifaximin in polymorphic form α to (D) rifaximin in polymorphic form δ is from 9:1 to 1:9; and
      one or more pharmaceutical excipient(s) selected from fillers, binders and disintegrants
      wherein the rifaximin in the pharmaceutical composition comprises less than about 5% of polymorph forms other than polymorphic a form and polymorphic form δ.

2. Pharmaceutical composition according to claim 1, wherein the molar ratio of (A) rifaximin in polymorphic form α to (D) rifaximin in polymorphic form δ is from 5:1 to 1:3.

3. Pharmaceutical composition according to claim 1, wherein the total amount of rifaximin is 550 mg, and wherein the composition comprises 45 wt. % to 75 wt. % of components (A) and (D), and 10 wt. % to 45 wt. % filler.

4. Pharmaceutical composition according to claim 3, wherein upon administration the $C_{max}$ of rifaximin is less than 1.5 ng/ml.

5. Pharmaceutical composition according to claim 4, wherein upon administration the AUC of rifaximin is less than 10 ng/ml×h.

6. Pharmaceutical composition according to claim 1, wherein the rifaximin contains water in an amount of 1.5 wt. % to 5 wt based on the total amount of rifaximin.

7. Pharmaceutical composition according to claim 1 comprising
45 wt % to 75 wt % of components (A) and (D), and
10 wt % to 45 wt % filler.

8. Pharmaceutical composition according to claim 1, wherein the filler is microcrystalline cellulose.

9. Pharmaceutical composition according to claim 1, wherein the pharmaceutical composition is present as an oral dosage form.

10. Oral dosage form according to claim 9, wherein the dosage form is packed in a co-extruded composite material having a water vapor permeability of less then 0.15 $g/m^2$/day determined according to ASTM F1249-13.

11. Method for preparing a tablet according to claim 9 comprising the steps of
(i) providing (A) rifaximin in polymorphic form α and (D) rifaximin in polymorphic form δ and optionally one or more further excipients
(ii) optionally dry granulating the mixture from step (i) and optionally one or more further excipients
(iii) compressing the mixture from step (i) or the granulates from step (ii) and optionally further excipients into a tablet,
(iv) optionally coating the tablet.

12. Method for preparing a tablet according to claim 9 comprising the steps of
(i') providing (A) rifaximin in polymorphic form α having a water content of 2 to 4.5 wt. % and optionally one or more further excipient(s),
(ii') optionally dry granulating the mixture of step (i') and one or more further excipients,
(iii') compressing the mixture from step (i') or the granules from step (ii') and optionally further excipients into a tablet and
(iv') storing the composition under sealed conditions at 25° C. for 2 to 3 months.

13. Method according to claim 11, wherein step (ii) or (ii') comprises compacting the mixture of step (i) or (i') to a slug and further granulating the slug.

* * * * *